United States Patent [19]

Uchikuga et al.

[11] 4,060,551
[45] Nov. 29, 1977

[54] METHOD OF PRODUCING PANTETHINE

[75] Inventors: Saburo Uchikuga, Yokohama; Masataka Kuroki, Sagamihara, both of Japan

[73] Assignee: Sogo Pharmaceutical Company Limited, Japan

[21] Appl. No.: 713,282

[22] Filed: Aug. 10, 1976

[30] Foreign Application Priority Data

May 25, 1976   Japan ............................ 51-059679

[51] Int. Cl.$^2$ .......................................... C07C 149/23
[52] U.S. Cl. ........................ 260/561 S; 260/561 B; 260/562 N
[58] Field of Search ............ 260/561 S, 562 N, 561 B

[56] References Cited

U.S. PATENT DOCUMENTS

| 2,625,565 | 1/1953 | Snell et al. | 260/561 S |
|---|---|---|---|
| 2,680,767 | 1/1954 | Snell et al. | 260/561S |
| 2,680,768 | 6/1954 | Snell et al. | 260/561 S |
| 3,300,508 | 1/1967 | Shimizu et al. | 260/561 S |

OTHER PUBLICATIONS

Ohta et al. Chem. Abstracts 64(1966) column 17710b.
Gross et al. Tetrahedron 24(1968) pp. 6935–6939.

*Primary Examiner*—Arthur P. Demers
*Attorney, Agent, or Firm*—Browdy and Neimark

[57] ABSTRACT

Salt of pantothenic acid and salt of cystamine or cysteamine are caused to react under the presence of an accelerator selected from the group consisting of carbodiimides and N-hydroxy compounds without any pretreatment thereby producing pantethine or pantetheine, and the pantetheine is oxidized to produce pantethine which is a precursor of co-enzyme A.

12 Claims, No Drawings

METHOD OF PRODUCING PANTETHINE

FIELD OF INVENTION

The present invention relates to a novel and useful method of producing pantethine or pantetheine very simply, in high purity and high yield rate.

BACKGROUND

Panthethine or pantetheine is a useful compound as a precursor of co-enzyme A which plays an important part in energy metabolism, lipid metabolism and acetylation reaction in vivo.

Heretofore, the following methods of synthesizing pantethine or pantetheine have been known:

A. Method in which pantothenic acid is once activated into the form of ester, azide and mixed anhydride etc., and thereafter condensed with cystamine or cysteamine (Japanese Patent Application Publications Nos. 77/55 and 467/58, U.S. Pat. No. 2,625,565).

B. Method in which ethyleneimide derivative of pantothenic acid is caused to open its ring by means of hydrogen sulfide etc. and is thereafter oxidized (Japanese Patent Application Publications Nos. 23934/68 and 24649/68).

C. Method of condensing alethine derivative and pantolactone (Japanese Patent Application Publication No. 4672/56).

D. Method in which pantothenonitrile and cystamine are caused to react resulting in the formation of thiazoline ring, and this is caused to open the ring, and oxidized (Japanese Patent Application Publications Nos. 10149/65, 13848/65 and 28929/65).

E. Method in which both or one of salts of pantothenic acid and cystamine are subjected to a pretreatment and thereafter condensed (Japanese Patent Application Publications Nos. 2896/66, 26490/72 and 3324/69, Japanese Patent Application Laying-Open Publication No. 76816/73).

These methods (A)-(D) require reactions of several stages from the starting materials to the products, and the refining in each stage and the product is very difficult and as a result it is inevitable that by-product in each reaction is mixed into the product resulting in making it difficult to obtain pantethine of high purity. In the method (E), it is necessary that both or one of the starting raw materials is in the form of liberation, and since the by-products which are difficult to be refined off are produced, satisfactory products in purity can not be obtained.

The above described prior art methods are not sufficiently satisfactory as industrial methods because of multi reaction stages, production of by-products in such a reaction, complication of production steps, use of special raw materials and secondary raw materials which can not be easily obtained, and difficulties such as lowering of product purity, etc.

SUMMARY

The present invention removes such drawbacks of the prior art methods, and it can use easily available raw materials and sub-materials, and can suppress production of by-products to as little as possible thereby easily obtaining pantethine of high purity in a high yield.

Namely, the present invention is characterized in that an alkali metal salt, alkaline earth metal salt or ammonium salt of pantothenic acid, mineral acid salf of cystamine or cysteamine, and a carbodiimide as a condensation agent are used, which are easily available in high purity, and the reaction is carried out in the presence of an N-hydroxy compound as reaction accelerator. Due to the presence of the condensation agent and accelerator, the above salts of raw materials can react very effectively and in a shorter period of time.

DETAILED DESCRIPTION OF EMBODIMENTS

The present invention comprises contacting two kinds of raw materials, condensation agent and accelerator and thereby effecting a dehydration condensation reaction, and in this method, for improvement of reaction velocity, a solvent is preferably used in the reaction system, and particularly for making a uniform system, mixed solvent is preferably used.

As the salt of pantothenic acid used in the reaction, various kinds of salts can be mentioned, and in general, alkali metal salts, alkaline earth metal salts and ammonium salts etc. are used. However from view points of industrial manufacture such as easy availability and high purity and so on, the use of calcium pantothenate is most advantageous. As salts of cystamine and cysteamine, various salts can be used, however mineral acid salts are generally preferred, and among them particularly hydrochloride and sulfate are preferably used from the viewpoint of their availability and high purity.

Carbodiimide is used as condensation agent. Various kinds of carbodiimides are possible. However from the viewpoint of availability, stability and easy separation of the produced urea derivative, the use of dicyclohexylcarbodiimide is most preferable.

As the accelerator, N-hydroxy compounds are used. In this respect, from the viewpoint of availability, stability, easy separation and acceleration of reaction, it is preferable to adopt 1-hydroxybenzatriazole and N-hydroxybenzatriazole.

In the present invention, if only the carbodiimide is used, the desired object can not be attained, namely, production of pantethine and pantetheine is scarcely recognized. Heretofore a method of producing pantethine using carbodiimide as a condensation agent between free pantothenic acid and free cysteamine had already been disclosed in Japanese Patent Application Publication No. 2896/66, and this method is shown in Example 1 of such Publication; in such process calcium pantothenate is changed to free pantothenic acid by means of cation-exchange resin, and cystamine dihydrochloride and cysteamine dihydrochloride are also changed to free cystamine and cysteamine by removing hydrochloric acid by sodium; and thereafter pantethine and pantetheine are synthesized by means of carbodiimide, so that the synthesis method is quite troublesome and the process results in low yield. Of course, even if carbodiimide is used, calcium pantothenate is difficult to directly react with cystamine hydrochloride or cysteamine hydrochloride (as they are), and pantethine or pantetheine is scarcely produced. The presence of condensation agent and accelerator is an indispensable combination, and in the case of condensation agent alone or in the case of accelerator alone, pantethine or pantetheine can not be practically produced.

Namely, the present invention relates to a method of producing pantethine or pantetheine wherein as raw materials, a calcium salt of pantothenic acid and a mineral acid salt of cystamine or cysteamine are used, which are easily available in high purity, and as a condensation agent dicyclohexylcarbodiimide is adopted, and also as accelerator N-hydroxy compound, particularly 1-hydroxybenzotriazole or N-hydroxysuccinimide used, and in the presence of such an accelerator the dehydrating condensation reaction is effected to produce pantethine or pantetheine.

The present invention has first succeeded in obtaining pantethine of pantetheine at a higher yield rate by causing the reaction of calcium pantothenate with a hydrochloride of cystamine or cysteamine as they are with the use of an accelerator selected from the group consisting of dicyclohexylcarbodiimide and N-hydroxy compound. As noted above, the method of the present invention is a method that is easy and remarkably economical, and quite different from the prior art methods and novel and useful.

The present invention is characterized in that as raw materials salts are used, and in the presence of dicyclohexylcarbodiimide dehydrating agent and an accelerator such as N-hydroxy compound, for example, 1hydroxybenzotriazole and N-hydroxysuccinimide etc., the reaction is effected. In the presence of these condensation agent and accelerator, the salts of raw materials can react effectively and in a shorter period of time.

The present invention comprises causing dehydrating condensation reaction under intimate contact of two kinds of raw materials, condensation agent and accelerator, and it is preferable to use solvent in the reaction system in order to improve reaction velocity thereof, and particularly for making homogeneous system a mixed solvent is preferably used.

As salt of pantothenic acid used in the reaction, various kinds of salts can be used, for example, salts of alkali metal and alkaline earth metal etc. can be used. However from the industrial viewpoint of easy availability, degree of purity and rate of yield and so on, the use of calcium salt is the best. As salt of cystamine or cysteamine, various kinds of salts can be used. However from the industrial viewpoint of easy availabity and increase of yield etc., particularly hydrochloride and sulfate are preferably used.

As condensation agent, dicyclohexylcarbodiimide is generally used. In the present invention, when only condensation agent such as dicyclohexylcarbodiimide is used, the desired object can not be attained, namely production of pantethine is scarcely recognized. The presence of both condensation agent and accelerator is indispensable and particularly there is an important significance in the point of the use of N-hydroxy compound, for example, 1-hydroxybenzotriazole and or N-hydroxysuccinimide etc. as an accelerator. In the case condensation agent alone is used, or accelerator alone is virtually used, production of pantethine is impossible. In the case of a combination other than dicyclohexylcarbodiimide + N-hydroxy compound (for example, 1-hydroxybenzatriazole and N-hydrozysuccinimide etc.) the, desired object can not be also attained.

As a solvent used in the reaction, any solvent used in usual condensation, dehydrating reaction can be used, and solvents of amide group and pyridine group, for example, dimethylformamide, pyridine and so on are preferable. Besides, a mixed solvent composed of these solvents, water and hydrocarbons may be used. The reaction is effected in a solvent such as noted above with the raw materials being reacted in the presence of the condensation agent and accelerator at a reaction temperature below 100° C, preferably at or below a room temperature. Time period required for the reaction is usually several hours.

After the completion of reaction, the objective compound is separated from the reaction mixture and refined according to normal treatments. For example, after the reaction, solvents are evaporated under a reduced pressure, and the residue is added to water and the resultant deposited insoluble matter is filtered off, and the deposit obtained by cooling is filtered off, and the filtrate thereof is washed several times by means of chloroform and ether etc., and the water layer thereof is passed through an ion-exchange resin column, and the eluted solution is concentrated to dryness. Thus refined pantethine or pantetheine is obtained as a colorless, glassy mass.

Generally, pantethine has been considered not to be pulverized, however the product refined according to the present invention, due to its high purity is easily pulverized by freeze drying thereof.

In the case pantetheine is obtained, it is subjected to oxidation treatment to change it into pantethine as desired. Solution of pantetheine is immediately oxidized into pantethine by adding oxidizing matter such as hydrogen peroxide, oxygen and so on. Also, pantetheine may be left in the atmosphere as it is so that it is catalytic oxidized by oxygen in the air thereby obtaining pantethine.

The obtained pantethine is subjected to the above described refining steps to obtain refined pantethine.

EXAMPLE 1

11.9g. of calcium pantothenate, 5.6g. of cystamine dihydrocloride and 7.7g. of 1-hydroxybenzotriazole were dissolved in a mixed solvent of 50ml. of pyridine, 10ml. of water and 25ml. of benzene, and thereafter pyridine (25ml.) solution of 10.5g. of dicyclohexylcarbodiimide was added thereto at a time, and then this was subjected to reaction at a temperature below 10° C for 1 hour and thereafter to reaction at a room temperature for 5 hours. Then the solvent was removed at a reduced pressure, and the residue thereof was added with 50ml. of water and the resultant deposited crystals were removed by filtration. Pyridine left in the filtered mother liquor was completely removed azeotropically with water. The residue thereof was added with 50ml. of water, and after cooling it, the deposited crystals was removed by filtration, and extracted two times with 20ml. of chloroform. The water layer was passed through a monobed column composed of 78ml. of strong acidic cation exchanger resin (Amberlite 1R-120B) [H+] and 150ml. of strong basic anion exchanger resin (Amberlite 1RA-410) [OH−], and washed out with water. The presence of the objective compound in the flowed out liquid was traced by refractometer. The eluted solution was concentrated under a reduced pressure and subjected to freeze drying, and thereby 9.6g. of pantethine in the form of pulverized crystal was obtained (69.2% yield).

In the thin layer chromatography, it coincided with the authentic sample.

Ultraviolet absorption spectrum: $\lambda_{max}^{H_2O}$ 245mμ

EXAMPLE 2

11.9g. of calcium pantothenate, 5.6g. of cystamine dihydrochloride and 7.7g. of 1-hydroxybenzotriazole were dissolved in 5ml. of dimethylformamide and 10ml. of water and dimethylformamide 25ml. solution of DCC 10.5g. was added therein at a time under ice cooling. The reaction was effected for 1 hour under agitation and thereafter for 5 hours at a room temperature, and then dimethylformamide was removed under a reduced pressure, and the residue thereof was added with 50ml. of water, and the deposited crystals were filtered out, and extracted two times with 20ml. of chloroform, and then passed through a monobedcolumn composed of 75ml. of strong acidic cation exchanger resin (Amberlite 1R-120B) [H] and 150ml. of strong basic anion exchange resin (Amberlite 1RA-410) [OH] and washed out with water. The presence of the objective compound in the flowed out liquid was traced by refractometer. By concentrating the flowed out liquid under a reduced pressure, colorless transparent viscos liquid of pantethine which was the objective compound was obtained. Drying was carried out by means of a vacuum dryer for one night and thereafter the dried product was weighed.

Pantethine was obtained at a yield of 11.3g. and a yield rate of 85%.

In the thin layer chromatography, it coincided with the authentic sample.

Ultraviolet absorption spectrum: $\lambda_{max}^{H_2O}$ 245M$\mu$

EXAMPLE 3

The same process as Example 2 was carried out except for substituting N-hydroxysuccinimide for 1-nydroxybenzatriazole dimethylformamide of Example 2.

Yield 9.5g., 68.5%.

In the thin layer chromatography, it coincided with the authentic sample.

Ultraviolet absorption spectrum: $\lambda_{max}^{H_2O}$ 245m$\mu$

The same process as Example 2 was carried out except for substituting 5.7g. of cysteamine hydrochloride for 5.6g. of cystamine dihydrochloride and pyridine for dimethylformamide and effecting reaction under nitrogen gas flow, and thereby 7.9g. (57%) of pantetheine was obtained.

In the thin layer chromatography, it coincided with the authentic sample.

EXAMPLE 5

7.6g. of pantetheine obtained in Example 4 was dissolved in 50ml. of water, and oxidized by 5% hydrogen peroxide under agitation and ice cooling. Thereafter it was subjected to ion exchange treatment refining, thereby obtaining 7.65g. (55%) of pantethine.

In the thin layer of chromatography, it coincided with the authentic sample.

Ultraviolet absorption spectrum: $\lambda_{max}^{H_2O}$ 245m$\mu$

EXAMPLE 6

11.9g. of calcium pantothenate, 6.8g. of cystamine dihydrochloride and 7.7g. of 1-hydroxylbenzotrizole were dissolved in 50ml. of pyridine and 10ml. of water, and thereafter pyridine (25ml.) solution of 10.5g. of dicyclohexylcarbodiimide was added thereto at a time, and the reaction was effected at a temperature below 10° C for 1 hour and then for 5 hours at a room temperature. Next the solvent was removed under a reduced pressure, the residue thereof was added with 50ml. of water, and the deposited crystals were removed by filtration. Pyridine left in the filtered mother liquor was completely removed azetropically with water. The residue thereof was added with 50ml. of water and after cooling, the deposited crystals were filtration removed and extracted with 20ml. of chloroform two times. The water layer was treated under a reduced pressure to remove the remaining chloroform, and thereafter like Example 1, passed through the ion exchange resin, and the flowed out liquid was concentrated under a reduced pressure and thereby colorless transparent viscous liquid of pantethine which was the objective compound was obtained. Drying was carried out by means of a vacuum dryer for one night and as a result 9.6g. of pantethine (yield rate 69.2%) was obtained.

In the thin layer chromatography, it coincided with the authentic sample.

Ultraviolet absorption spectrum: $\lambda_{max}^{H_2O}$ 245m$\mu$

Referential Example

Production of pantethine by removing N-hydroxy compound from reaction system;

11.916g. of calcium pantothenate and 5.629g. of cystamine dihydrochloride were dispersed in 100ml. of dimethylformamide, and dimethylfromamide 50ml. solution of 10.429g. of dicyclohexylcarbodiimide was poured therein at a time under ice cooling, and the reaction was effected for 2 hours under agitation and then for 1 hour at a room temperature, and thereafter the reaction solution was left as it was for one night, and then dimethylformamide was removed under a reduced pressure. The residue was added with 100ml. of water and the deposited crystals were filtration removed, and then extraction with 50ml. of chloroform was carried out two times, and thereafter the water layer was concentrated to about 50ml. under a reduced pressure. The resultant concentrated liquid was passed through a monobed column composed of 100ml. of strong acidic cation exchanger resin (Amberlit 1R-120B) [H+] and 100ml. of strong basic anion exchanger resin (Amberlite 1RA-410) [OH−], and washed out with water. The presence of the objective compound in the flowed out liquid was traced by refractometer. About 400ml. of the eluted solution was concentrated under a reduced pressure, and thereby colorless transparent viscos liquid of pantethine which was the objective compound was obtained. This was dried in a silica gel vacuum desiccator for one night.

Yield 0.07g. (0.5%)

What is claimed is:

1. A method of producing pantethine comprising reacting a salt of pantothenic acid and a salt of cystamine in the presence of a carbodiimide and an N-hydroxy compound selected from the group consisting of 1-hydroxybenzotriazole and N-hydroxysuccinimide.

2. A method as claimed in claim 1, wherein said salt of pantothenic acid is selected from the group consisting of alkali metal salt, alkaline earth metal salt and ammonium salt.

3. A method as claimed in claim 1, wherein said salt of cystamine is a mineral acid salt.

4. A method in accordance with claim 1 wherein said carbodiimide is dicyclohexylcarbodiimide.

5. A method in accordance with claim 2 wherein said salt of pantothenic acid is calcium salt, sodium salt or ammonium salt.

6. A method in accordance with claim 3 wherein said salt of cystamine is dihydrochloride salt or sulfate salt.

7. A method as claimed in claim 2, wherein said salt of cystamine and salt of cysteamine are mineral acid salts.

8. A method of producing pantethene comprising reacting a salt of pantothenic acid and a salt of cysteamine in the presence of carbodiimide and an N-hydroxy compound selected from the group consisting of 1-hydroxybenzotriazole and N-hydroxysuccinimide to product pantethenine, and oxidizing said pantethenine to product pantethene.

9. A method as claimed in claim 8, wherein said salt of pantothenic acid is the one selected from the group consisting of calcium salt, sodium salt and ammonium salt.

10. A method as claimed in claim 8, wherein said salt of cysteamine are the ones selected from the group consisting of hydrochloride and sulfate salts.

11. A method as claimed in claim 8, wherein said carbodiimide is dicyclohexylcarbodiimide.

12. A method of producing pantethine comprising causing a salt of pantothenic acid selected from the group consisting of calcium salt sodium salt and ammonium salt to react with a salt selected from the group consisting of hydrochloride and sulfate of cystamine or of cysteamine in the presence of dicyclohexylcarbodiimide and a N-hydroxy compound selected from the group consisting of 1-hydroxybenzotriazole and N-hydroxysuccinimide.

* * * * *

UNITED STATES PATENT AND TRADEMARK OFFICE
CERTIFICATE OF CORRECTION

PATENT NO. : 4,060,551
DATED : November 29, 1977
INVENTOR(S) : UCHIKUGA et al

It is certified that error appears in the above-identified patent and that said Letters Patent are hereby corrected as shown below:

Claim 8, line 1, "pantethene" should read --pantethine-- claim 8, line 6, "pantethenine" should read --pantetheine-- claim 8, line 7, "nine" should read --ine--; "pantethene" should read --pantethine-- claim 8, lines 6 and 7, change "product" to --produce--

Signed and Sealed this

Twenty-fourth Day of July 1979

[SEAL]

Attest:

LUTRELLE F. PARKER

Attesting Officer  Acting Commissioner of Patents and Trademarks